United States Patent [19]

Atallah

[11] Patent Number: 5,674,202
[45] Date of Patent: Oct. 7, 1997

[54] MEDICAL IMPLEMENT HOLDER AND METHOD OF SUPPORTING MEDICAL IMPLEMENT

[76] Inventor: M. William Atallah, 429 Bayridge Pkwy., Brooklyn, N.Y. 11209

[21] Appl. No.: 443,123

[22] Filed: May 17, 1995

[51] Int. Cl.⁶ ................................................. A61M 5/32
[52] U.S. Cl. ........................ 604/174; 128/DIG. 26
[58] Field of Search ..................... 482/92, 93, 105; 604/174, 179, 180; 128/DIG. 26

[56] References Cited

U.S. PATENT DOCUMENTS

| | | | |
|---|---|---|---|
| 3,532,339 | 10/1970 | Smith | 482/105 |
| 3,972,321 | 8/1976 | Proctor | 604/169 |
| 3,977,407 | 8/1976 | Coleman et al. | 604/179 |
| 4,239,211 | 12/1980 | Wilkerson | 482/105 |
| 4,396,190 | 8/1983 | Wilkerson | 482/105 |
| 4,623,143 | 11/1986 | Wuellenwabar | 482/105 |
| 4,692,358 | 9/1987 | Westplate | 482/105 X |
| 4,798,497 | 1/1989 | Bloos | 484/105 X |

FOREIGN PATENT DOCUMENTS

| 124874 | 3/1946 | Switzerland | 604/179 |
|---|---|---|---|

*Primary Examiner*—Sam Rimell
*Attorney, Agent, or Firm*—Ostrolenk, Faber, Gerb & Soffen, LLP

[57] ABSTRACT

Apparatus for holding a medical implement in position in a body opening. The apparatus includes a strap of material, the strap of material having a length and two ends, a weight being provided at each of the two ends, the strap of material being draped over the body of a patient in such a way that the medical implement is supported from below by a portion of this strap of material intermediate the ends, the weight at the ends of the material counter-balancing the tendency of the medical implement to move or fall downwardly out of the body opening.

15 Claims, 1 Drawing Sheet

5,674,202

1

MEDICAL IMPLEMENT HOLDER AND METHOD OF SUPPORTING MEDICAL IMPLEMENT

BACKGROUND OF THE INVENTION

The present invention relates to a medical device and, in particular, to a device for retaining a cystoscope or other surgical or medical instrument in position in a body opening.

A common problem in connection with the insertion of cystoscopes into body openings, for example, into the urethra, is that the cystoscope will tend to fall or move out of the body opening due to its weight. The physician necessarily has to hold the cystoscope in position to keep it from moving or falling out or have an assistant attend to holding the cystoscope.

SUMMARY OF THE INVENTION

It is, accordingly, an object of the present invention to provide a holder for a medical device which is inserted into a body opening.

In particular, it is an object of the present invention to provide a holder for holding a cystoscope in a body opening, for example, the urethra.

The above and other objects of the present invention are achieved by a holding device for preventing a medical implement from moving or falling out of a body opening due to its own weight comprising a strap of material, the strap of material having a length and two ends, a weight being provided at each of the two ends, the strap of material being draped over the body of a patient in such a way that the medical implement is supported from below by a portion of the strap of material intermediate the ends, the weight at the ends of the material counter-balancing the tendency of the medical implement to move or fall downwardly out of the body opening.

The above and other objects of the invention are also achieved by a method for holding a medical implement in position in a body opening comprising inserting the medical implement into the body opening, providing a strap of material, the strap of material having a length and two ends, a weight being provided at each of the two ends draping the strap of material over the body of a patient in such a way that the medical implement is supported from below by a portion of the strap of material intermediate the ends, with the weight at the ends of the material counter-balancing the tendency of the medical implement to move or fall downwardly out of the body opening.

Other objects, features and advantages of the present invention will be apparent from the detailed description which follows.

BRIEF DESCRIPTION OF THE DRAWINGS

The invention will be described in greater detail in the following detailed description with reference to the drawings in which.

DETAILED DESCRIPTION OF THE INVENTION

Figure 1:
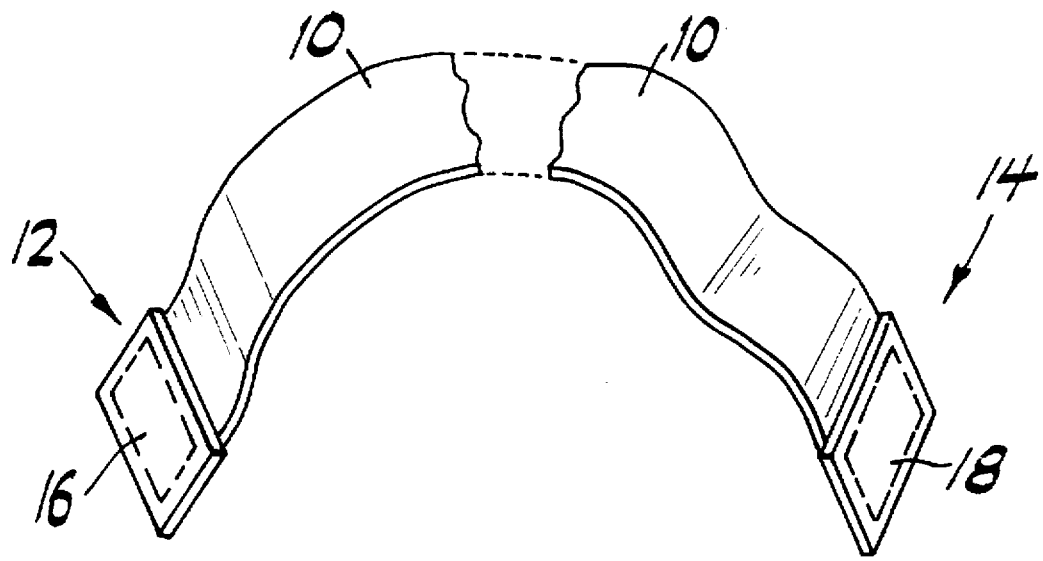
FIG. 1 shows a perspective drawing of the medical implement holder according to the present invention.

With reference now to the drawings, the invention comprises a length of strap material 10, shown in perspective view in FIG. 1. The length of material 10 is sufficiently long so that it can be draped over the patient's body as will be described below with reference to FIG. 2. A suitable length has been found to be, for example 50 inches, but this can be varied as needed. At each of the ends 12 and 14 of the strap of material 10, the material is formed in the shape of a pouch or closed space holding a respective weight 16 and 18, shown schematically in FIG. 1. The weight may be, for example, a suitable metal. The strap of material 10 may be any suitable material, for example, any cloth, synthetic plastic material, etc. Any foldable material which can be easily draped over the patient's body is acceptable.

Figure 2:
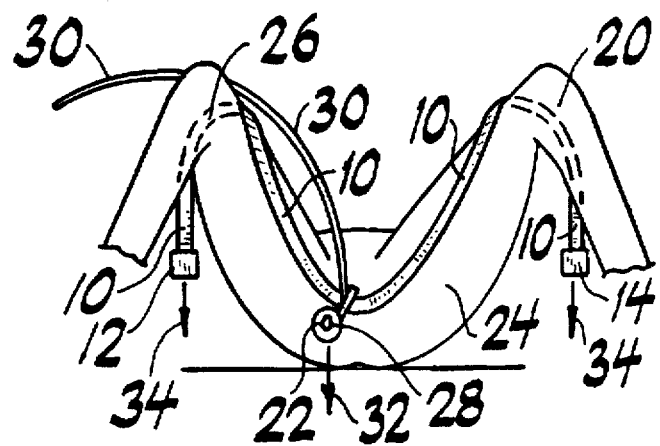
FIG. 2 shows the medical implement holder of the present invention in use.

FIG. 2 shows the invention in use. The patient is indicated at 20 in a lithotomy or reclined position. In a typical operation, a cystoscope 22 is inserted into the urinary canal. The patient's legs are shown at 24 and 26. The cystoscope 22 generally has a telescopic opening 28 for observation of the bladder and urethra canal and may include a tube 30 as known in the art, for example, a fiber optic cable and irrigation canal, as conventionally known.

In practice, the cystoscope is inserted into the urinary canal opening, but tends to fall downwardly in the direction of arrow 32 due to its own weight. The cystoscope holder of the invention is used by placing the strap of material 10 at its intermediate portion beneath the cystoscope 22 to support the cystoscope 22. Strap portions 10 are then draped over the patients legs, as shown, with the ends 12 and 14 providing a counter-balancing weight downwardly extending in the direction of arrows 34 which counter-balances the tendency of the cystoscope 22 to move downwardly in the direction of arrow 32 due to its own weight.

The device of the invention can be made in a reusable or disposable form. Typically, it would be disposable. Also the strap material 10 may be made of a high friction material or be coated on at least one side with a high friction material so that it will not easily slide on the patient's body or on a surgical drape. For example, in FIG. 2, when the strap is draped over the user's legs or a surgical drape covering the legs, the friction material will serve to prevent the strap from sliding.

Although the present invention has been described in relation to particular embodiments thereof, many other variations and modifications and other uses will become apparent to those skilled in the art. Accordingly, the present invention should be limited not by the specific disclosure herein, but only by the appended claims.

What is claimed is:

1. Apparatus for holding a medical implement in position in a body opening comprising:

a flexible strap of material, the strap of material having a length and two end portions, a weight being provided at each of the two end portions, the two weights being separate from each other, the two end portions defining a middle portion of the strap between the end portions, the strap of material being adapted to be draped over the body of a patient such that the middle portion depends downwardly with an approximately central section of the middle portion forming a lowest point of the middle portion, the medical implement being supported from below by the central section, the end portions depending downwardly from the middle portion, the middle portion of the strap not being weighted to overcome the weight of the two weights at the end portions, the weight at each end portion of the strap of material being adapted to counter-balance the tendency of the medical implement held by the middle portion of the strap to move or fall downwardly out of the body opening.

2. The apparatus of claim 1, wherein the apparatus is adapted for holding a medical implement comprising a cystoscope in the urethra.

3. Apparatus for holding a medical implement in position in a body opening comprising:

a flexible strap of material, the strap of material having a length and two end portions, a weight being provided at each of the two end portions, the two weights being separate from each other, the two end portions defining a middle portion of the strap between the end portions, the strap of material being adapted to be draped over the body of a patient such that the middle portion depends downwardly with an approximately central section of the middle portion forming a lowest point of the middle portion, the medical implement being supported from below by the central section, the end portions depending downwardly from the middle portion, the middle portion of the strap not being weighted to overcome the weight of the two weights at the end portions, the weight at each end portion of the strap of material being adapted to counter-balance the tendency of the medical implement held by the middle portion of the strap to move or fall downwardly out of the body opening;

the strap of material comprising a strap provided on the patient so as to support the medical implement such that the strap of material is draped upwardly around the patient's legs and then downwardly with the weighted end portions exerting downward force which tends to counter-balance the weight of the medical implement.

4. The apparatus of claim 1, wherein the weight comprises metal.

5. The apparatus of claim 1, wherein the strap of material is selected from the group consisting of a cloth, synthetic polymer and a combination of these materials.

6. The apparatus of claim 1, wherein the strap of material comprises a friction material or is coated on at least one side with a friction material.

7. A method for holding a medical implement in position in a body opening during a surgical procedure comprising:

inserting the medical implement into the body opening;

providing a strap of material, the strap of material having a length and two ends, a weight being provided at each of the two ends; and draping the strap of material over the body of a patient such that the medical implement is supported from below by a portion of the strap of material intermediate the ends, with the weight at each end of the material counter-balancing the tendency of the medical implement to move or fall downwardly out of the body opening, the strap not being fixedly attached to the body of the patient and being slidably movable with respect to the body of the patient.

8. The method of claim 7, wherein the medical device comprises a cystoscope and the body opening comprises the urethra.

9. A method for holding a medical implement in position in a body opening comprising:

inserting the medical implement into the body opening;

providing a strap of material, the strap of material having a length and two ends, a weight being provided at each of the two ends;

draping the strap of material over the body of a patient such that the medical implement is supported from below by a portion of the strap of material intermediate the ends, with the weight at each end of the material counter-balancing the tendency of the medical implement to move or fall downwardly out of the body opening; and further comprising providing the strap of material on the patient so as to support the medical implement such that the strap of material is draped upwardly around the patient's legs and then downwardly with the weighted ends exerting downward force which tends to counter-balance the weight of the medical implement.

10. A method for holding a medical implement in position in a body opening comprising:

inserting the medical implement into the body opening;

providing a strap of material, the strap of material having a length and two ends, a weight being provided at each of the two ends;

draping the strap of material over the body of a patient such that the medical implement is supported from below by a portion of the strap of material intermediate the ends, with the weight at each end of the material counter-balancing the tendency of the medical implement to move or fall downwardly out of the body opening; and wherein the weight comprises metal.

11. The method of claim 7, wherein the step of providing a strap of material comprises providing a strap of material selected from the group consisting of a cloth, synthetic polymer and a combination of these materials.

12. The method of claim 7, further comprising providing said strap of material as a friction material or with a coating on at least one side of a friction material.

13. A method for holding a medical implement in position in a body opening comprising:

inserting the medical implement into the body opening;

providing a strap of material, the strap of material having a length and two ends, a weight being provided at each of the two ends;

draping the strap of material over the body of a patient such that the medical implement is supported from below by a portion of the strap of material intermediate the ends, with the weight at each end of the material counter-balancing the tendency of the medical implement to move or fall downwardly out of the body opening, the strap not being fixedly attached to the body of the patient; and further comprising providing the strap of material on the patient such that the strap of material supports the medical implement, the strap of material being draped upwardly around the patient's legs and then downwardly with the weighted ends exerting downward force which tends to counter-balance the weight of the medical implement.

14. Apparatus for holding a medical implement in position in a body opening during a surgical procedure comprising:

a flexible strap of material, the strap of material having a length and two end portions, a weight being provided at each of the two end portions, the two weights being separate from each other, the two end portions defining a middle portion of the strap between the end portions, the strap of material being adapted to be draped over the body of a patient such that the middle portion depends downwardly with an approximately central section of the middle portion forming a lowest point of the middle portion, the medical implement being supported from below by the central section, the end portions depending downwardly from the middle portion, the middle portion of the strap not being weighted to overcome the weight of the two weights at the end portions, the weight at each end portion of the strap of material being adapted to counter-balance the tendency of the medical implement held by the middle portion of the strap to move or fall downwardly out of the body opening, the strap not being fixedly attachable to the body of the patient and being slidably movable with respect to the body of the patient.

15. A method for holding a medical implement in position in a body opening comprising:

inserting the medical implement into the body opening;

providing a strap of material, the strap of material having a length and two ends, a weight being provided substantially only at each of the two ends; and draping the strap of material over the body of a patient such that the medical implement is supported from below by a portion of the strap of material intermediate the ends, with the weight at each end of the material counter-balancing the tendency of the medical implement to move or fall downwardly out of the body opening.

\* \* \* \* \*